(12) United States Patent
Seryczynski

(10) Patent No.: US 12,196,215 B2
(45) Date of Patent: Jan. 14, 2025

(54) CENTRIFUGAL PUMP AND METHOD FOR STATUS DETECTION OF A CENTRIFUGAL PUMP

(71) Applicant: KSB SE & Co. KGaA, Frankenthal (DE)

(72) Inventor: Jakub Seryczynski, Frankenthal (DE)

(73) Assignee: KSB SE & Co. KGaA, Frankenthal (DE)

( * ) Notice: Subject to any disclaimer, the term of this patent is extended or adjusted under 35 U.S.C. 154(b) by 420 days.

(21) Appl. No.: 17/595,892

(22) PCT Filed: Jun. 17, 2020

(86) PCT No.: PCT/EP2020/066721
§ 371 (c)(1),
(2) Date: Nov. 29, 2021

(87) PCT Pub. No.: WO2020/254380
PCT Pub. Date: Dec. 24, 2020

(65) Prior Publication Data
US 2022/0235788 A1    Jul. 28, 2022

(30) Foreign Application Priority Data
Jun. 18, 2019    (DE) ..................... 10 2019 004 263.8

(51) Int. Cl.
*F04D 27/00* (2006.01)
*A61M 60/148* (2021.01)
(Continued)

(52) U.S. Cl.
CPC ......... *F04D 27/001* (2013.01); *A61M 60/148* (2021.01); *A61M 60/422* (2021.01);
(Continued)

(58) Field of Classification Search
CPC ............... A61M 60/148; A61M 60/422; F04D 15/0088; F04D 13/06; F04D 1/00;
(Continued)

(56) References Cited

U.S. PATENT DOCUMENTS

| 4,990,794 A * | 2/1991 | Ferrari ............... G01N 21/4738 250/227.25 |
| 7,963,423 B2 * | 6/2011 | Sassner .................. B67D 7/222 222/14 |
| 9,616,157 B2 * | 4/2017 | Akdis ................. F04D 29/0473 |
| 2018/0033129 A1 | 2/2018 | Finn et al. |

FOREIGN PATENT DOCUMENTS

| EP | 2 538 085 A2 | 12/2012 |
| JP | 2010-101192 A | 5/2010 |

(Continued)

OTHER PUBLICATIONS

International Search Report (PCT/ISA/210) issued in PCT Application No. PCT/EP2020/066721 dated Sep. 16, 2020 with English translation (five (5) pages).

(Continued)

*Primary Examiner* — Peter J Bertheaud
(74) *Attorney, Agent, or Firm* — Crowell & Moring LLP

(57) ABSTRACT

A pump arrangement for conveying a liquid, in particular for conveying waste water or service water, includes a pump housing and an impeller rotatably arranged in the pump housing about a rotation axis for conveying the liquid. At least one sensor, in particular a 3D sensor, is present for detecting a surface of the impeller to sense an extent of build-up on the impeller. The at least one sensor is arranged on and/or in the pump housing.

19 Claims, 3 Drawing Sheets

(51) Int. Cl.
    *A61M 60/422*     (2021.01)
    *F04D 1/00*     (2006.01)
    *F04D 13/06*     (2006.01)
    *F04D 15/00*     (2006.01)
    *F04D 29/08*     (2006.01)
    *F04D 29/22*     (2006.01)
    *F04D 29/42*     (2006.01)
    *G01S 13/34*     (2006.01)

(52) U.S. Cl.
CPC ............... *F04D 1/00* (2013.01); *F04D 13/06* (2013.01); *F04D 15/00* (2013.01); *F04D 15/0066* (2013.01); *F04D 15/0088* (2013.01); *F04D 29/086* (2013.01); *F04D 29/22* (2013.01); *F04D 29/426* (2013.01); *G01S 13/34* (2013.01)

(58) Field of Classification Search
CPC .... F04D 15/00; F04D 29/426; F04D 15/0066; F04D 29/086; F04D 27/001; F04D 29/22
See application file for complete search history.

(56) References Cited

FOREIGN PATENT DOCUMENTS

| WO | WO 2008/119931 A1 | 10/2008 | |
| WO | WO-2018122016 A1 * | 7/2018 | ............. F04D 13/06 |

OTHER PUBLICATIONS

German-language Written Opinion (PCT/ISA/237) issued in PCT Application No. PCT/EP2020/066721 dated Sep. 16, 2020 (six (6) pages).

German-language Office Action issued in German Application No. 10 2019 004 263.8 dated Jun. 17, 2021 (eight (8) pages).

International Preliminary Report on Patentability (PCT/IB/338 & PCT/IB/373) issued in PCT Application No. PCT/EP2020/066721 dated Dec. 30, 2021, including English translation (German-language Written Opinion (PCT/ISA/237) filed on Nov. 29, 2021) (eight (8) pages).

* cited by examiner

CENTRIFUGAL PUMP AND METHOD FOR STATUS DETECTION OF A CENTRIFUGAL PUMP

BACKGROUND AND SUMMARY OF THE INVENTION

The present invention relates to a centrifugal pump and a method for detecting the status of a centrifugal pump.

Centrifugal pumps are used in a plurality of applications for conveying a liquid. Particularly in the case of process water or waste water, the fluid being conveyed frequently contains impurities which can, under certain circumstances, lead to a blockage or unwanted impairment of the pump operation. This typically involves foreign elements becoming wrapped around an axle or the blades of the impeller, so that the efficiency of the pump arrangement diminishes. In extreme cases, the wrapping of foreign matter around the center of rotation of the impeller can lead to a blockage or the like.

A method for detecting an unwanted state of this kind, in which the power consumption of the pump is monitored and deviations from a standard value are assumed to indicate a blockage, is known from the prior art, for example from WO 2008/119931 A2.

The aim of the present invention is to provide the simplest and most reliable status detection possible for centrifugal pumps, so that imminent blockage states can be identified in good time and appropriate counter-measures taken.

This can be achieved with a pump arrangement which exhibits all the features of claim 1 or with the help of a method which executes all the method steps as claimed in claim 11.

Further advantageous embodiments of the invention or modifications of the method are contained in the dependent claims in each case.

The pump arrangement for conveying a liquid, in particular for conveying waste water or process water, comprises a pump housing and an impeller rotatably arranged in the pump housing for conveying the liquid. The invention is characterized in that there is at least one sensor, in particular a 3D sensor, for capturing the surface of the impeller, this at least one sensor being arranged on and/or in the pump housing.

By providing a sensor, the detection range of which is directed at the impeller, a particular portion of the impeller can be recorded continuously or intermittently. With the help of an analysis unit which analyzes the images recorded by the sensor, the presence of an error state, such as an imminent blockage or already advanced plaiting, can be inferred.

The optional 3D functionality enables the sensor to obtain information on objects which are adhering or are located upstream of the impeller, so that reliable assumptions can be made as to the existence of unwanted objects.

Since it is not unusual, particularly when conveying process water or even waste water, for relatively small or also relatively large objects of solid form to be carried along in the liquid thereby being conveyed, the one-off detection of an object of this kind upstream of the impeller will not usually lead to an error scenario. Instead, it is characteristic of plaiting in this case for a solid body to conceal the same, or a similar, region of a surface of the impeller over multiple rotations, and not to have been discharged with the pumped liquid.

According to a development of the invention, it may be provided that the sensor is designed to determine a distance from the impeller, preferably with the help of the time-of-flight technology (also: ToF technology).

ToF technology is essentially based on measurement of the time taken to travel by an emitted signal, so that by means of the signal travel time measured of the emitted signal, the distance of an object from the origin of a signal can be calculated almost exactly. This method is very advantageous in the present case, as it provides particularly resistant sensors for ToF technology, which are suitable for installation in a centrifugal pump and are able to withstand the adverse conditions prevailing there.

As has already been briefly explained above, determining the distance between the sensor and impeller, or an object adhered thereto, provides an actual opportunity of detecting the presence of objects that have been carried along around the center of rotation of the impeller.

As an advantageous alternative, it may be provided that the sensor is designed to measure a distance from the impeller with the help of the phase-difference method.

A further advantageous alternative is frequency-modulated continuous-wave technology (FMCW or frequency-modulated continuous wave).

According to an optional modification of the present invention, it may be provided that the sensor is an optical sensor, an optical 2D sensor, an optical 3D sensor, a 2D ultrasound sensor, a 3D ultrasound sensor, a MIMO (multiple-input multiple-output) radar sensor, a 2D laser distance sensor and/or a 3D laser distance sensor, preferably based on the triangulation principle.

According to a preferred embodiment of the invention, the impeller may be provided with a characteristic pattern on its surface, which can be detected by the sensor in a particular rotational position of the impeller; the pattern in this case is preferably a 2D pattern or a 3D pattern.

By applying a pattern to the impeller, it can be made easier for the sensor to optically capture a particular region of the impeller or the analysis of images produced by the sensor is thereby made easier. Hence, a characteristic pattern adapted to the type of sensor used can be identified far more easily, even if the images taken have not been produced under optimal conditions, or it is partially concealed by parts present in the liquid being conveyed. Hence, the fluid being conveyed is typically mixed with absorbing particles which impair the quality of the image. In addition, despite a possible illumination of the region of the impeller being inspected, if the fluid being conveyed is murky or dirty this can detract from the image quality significantly. It is advantageous in this case for the characteristic pattern to be used, since it makes it easier to draw a substantially better conclusion about the existence of blockages, or the like, even under sub-optimal conditions.

Consequently, it may also be provided that in addition there is a lighting means in and/or on the pump housing to illuminate a detection range of the sensor.

This is particularly helpful in the case of an optical sensor which requires sufficient light in order to capture an optical image.

According to an optional modification of the invention, it may be provided in this case that the lighting means is designed to emit intermittent light impulses, wherein the intermittently emitted light impulses are synchronized with a pump speed.

This means that the light impulse can only be produced when the region of the impeller which is of interest is located within the detection range of the sensor and is deactivated again after this region has been left. The lighting of the photo region is preferably coupled to the pump speed, so that no complicated control system is required.

In addition, it may be provided according to the invention that there is a micro-pump for rinsing a sensor surface of the sensor, so that residues accumulating in front of the sensor surface are actively removed. This micro-pump is a component arranged inside the pump housing which selectively guides to the sensor surface of the sensor a partial quantity of the liquid of the pump being conveyed, for example, so that no unwanted deposits can become attached there. Alternatively, the exposure of the sensor surface does not take place continuously but only as required. The micro-pump is therefore ultimately designed to clean the sensor surface, so that no detrimental residues can accumulate there or residues which are already present can be removed. The micro-pump may, however, also be integrated in the sensor.

A further alternative or additional possibility for keeping the sensor surface clear is provided with the help of an ultrasound micro-actuator which is designed to start an ultrasound shaking motion in an outside housing or a sensor surface of the sensor. This means that a layer of dirt which is deposited thereupon is broken up or a layer of dirt is prevented from forming in the first place. The deposition of unwanted residues on the surface of the sensor is also thereby prevented.

According to the invention, it may further be provided that the pump has an intake connection for drawing in the liquid being conveyed, in particular the waste water or the process water, and a further supply connection on the suction side of the pump for supplying clean water, so that any possible murkiness in the fluid being conveyed is reduced, at least briefly, in the region of the impeller. The murkiness of the liquid flowing through the pump often impedes the efficiency of the sensor, as the images taken by it are unusable, or only have limited use. However, so that a status detection still works perfectly, even when the liquid is very dirty, it is provided that in addition to the intake connection for drawing in the liquid being pumped, there is a supply connection arranged on the suction side of the pump via which a clear liquid, for example clear water, is introduced into the pump where necessary, for example while or just before a photo is taken by the sensor. This causes the murkiness of the liquid to be reduced temporarily, at least while the photo is being taken by the sensor, so that the images taken during this time have greater informational value.

According to a development of the invention, it may be provided that the supply connection is designed to supply a clear liquid, depending on the pump speed. This means that when an image is taken by the sensor, the clear liquid leads to a reduction in murkiness around the photo region and better images can therefore be taken.

It is therefore advantageous overall for a further supply connection for rain water, or the like, to be provided alongside the intake connection.

It is advantageous in this case for the supply connection to be attached in the pump housing too, as it means that the distance from the photo region is small and a supplied clear liquid has not yet been mixed in to the extent that would have been the case if the supply connection were arranged further away.

In addition, it may be provided according to the invention that a control unit is present which is connected to the sensor and is designed to analyze image data received from the sensor and to infer from this that there is a fault, in particular a blockage, plaiting, cavitation, mechanical damage and/or vibrations.

This happens, for example, when it is detected in the image that the impeller cannot be seen, for example, but an object arranged between the impeller and sensor.

It is preferably provided that the analysis of a photo taken by the sensor is performed with the help of artificial intelligence, preferably based on deep learning. This improves the reliability when detecting an imminent or already present error state, such as plaiting or a blockage.

The invention also relates to a method for detecting a blockage in a centrifugal pump, in particular in a centrifugal pump according to one of the previously described variants, wherein in the method the sensor produces images of the impeller and the data or images of the impeller produced by the sensor are analyzed by a control unit, in order to infer a fault, in particular a blockage, plaiting, cavitation, mechanical damage and/or vibrations.

The advantage of this new formulation is that the components for automated image processing are reasonably priced and very efficient and it is no longer necessary—as is customary in the prior art—for an independent logic system to be created which monitors the power uptake of the pump for deviations.

According to a development of the invention, it may be provided that before images of the impeller are captured, a clear liquid, for example clean water, is added on the suction side of the pump, in order to reduce any murkiness in the liquid present in the vicinity of the impeller for the time the images are taken.

It may preferably be provided that the images taken by the sensor reproduce a particular region of the impeller which is provided with a characteristic pattern, so that the assessment of the presence of a blockage or plaiting is easier to carry out, since the pattern cannot be identified in such a case, or only with some difficulty. For this purpose, a special 2D or 3D pattern can be applied to the impeller, so that the images are easier to analyze.

In addition, it may be provided in the method that the capture of the images is synchronized with the speed of the impeller, so that a particular portion, or multiple particular portions, of the impeller can be continuously captured using the sensor preferably in an intermittent manner.

Furthermore, before a photo is taken, the region of the impeller being captured can be illuminated using a light source, so that the images allow improved and easier analysis, in particular when the sensor is reset as an optical sensor.

According to the invention, it can further be provided that activities of a staff member operating the pump, such as the switching-on or off of the pump and/or an error acknowledgement, can be monitored with the help of the sensor, in order to obtain a more reliable current state of the pump.

This is particularly important in reducing an overall error probability, in which broken sensors frequently reproduce the current state incorrectly. The probability of this is further reduced by the method according to the invention.

Further advantages, details and features are evident from the following description of the figures.

DETAILED DESCRIPTION

Figure 1:
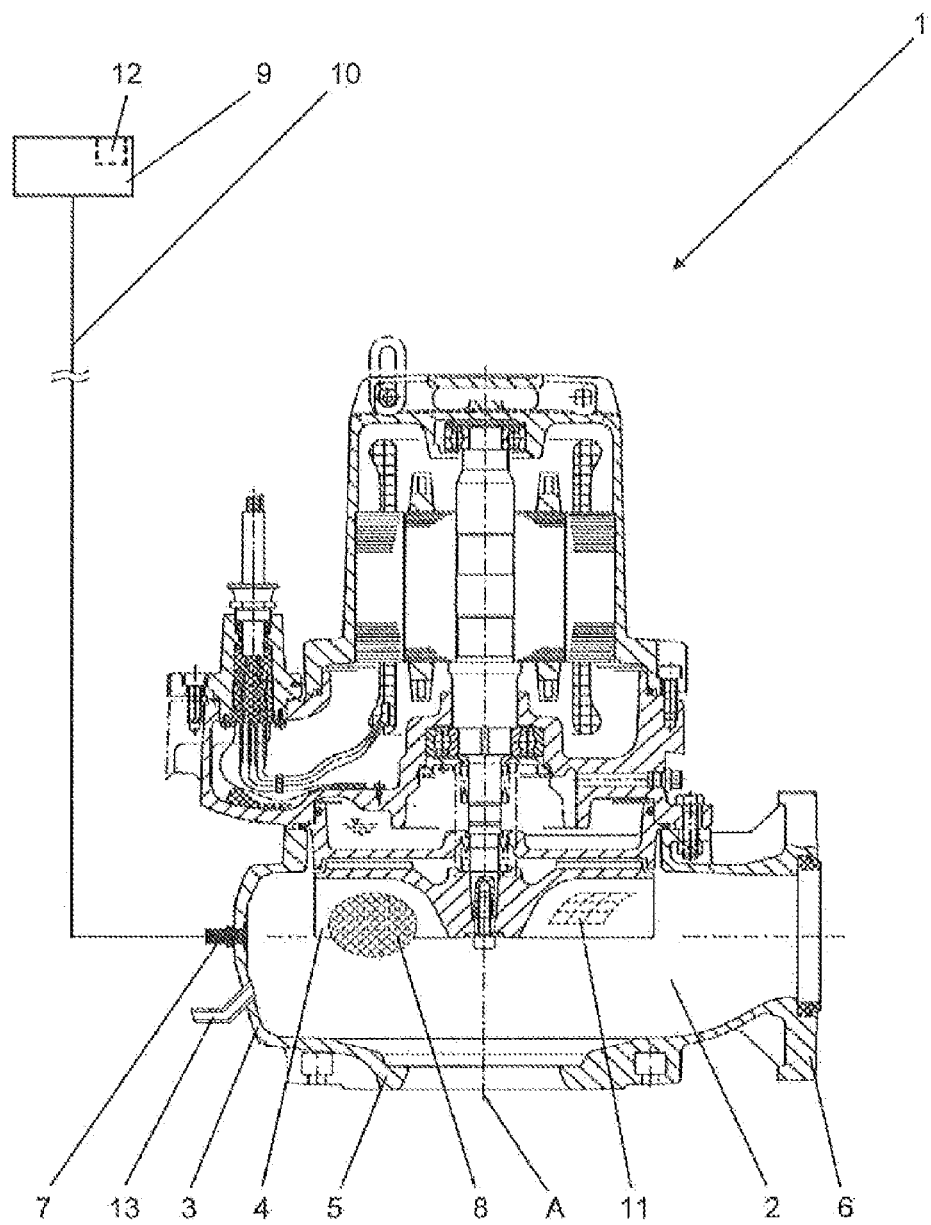
FIG. 1 shows a sectional view of a pump arrangement according to an embodiment of the invention with the sensor.

FIG. 1 shows a vertically installed pump arrangement 1 having a pump housing 3 exhibiting a flow chamber 2 and an impeller 4 arranged therein which, when rotating about its center of rotation A, conveys a liquid from its intake connection 5 to its delivery connection 6.

In addition, a sensor 7 is provided in and/or on the pump housing 3 which is oriented to a surface of the impeller 4. The sensor 7 is therefore able to detect whether an object 8 arranged upstream of the impeller surface is present which reduces the efficiency of the pump 1. Typically, an imminent blockage of the pump 1 can thereby be detected or plaiting inferred.

Plaiting in this case means the adhesion of a solid body 8 to the impeller 4, which is not released on the delivery side, even with constant rotation. Permanent carrying-along with the liquid being conveyed causes other free-floating elements to become attached thereto, so that the plait grows and the efficiency of the pump 1 is increasingly impeded. This can sometimes lead to a complete blockage of the pump 1.

In order to identify this kind of state as early as possible, the images or information captured by the sensor 7 are sent to a control unit 9 via a cable 10 or also wirelessly, so that a corresponding analysis can take place. This advantageously happens with the help of artificial intelligence, wherein deep-learning technology can also be utilized this case.

In this case, the anticipated image of the impeller surface is compared with the actual image, and it is possible to deduce from this whether there is any plaiting or even a blockage.

In order to obtain a better comparison, a pattern 11 has been applied to the surface of the impeller 4 in the embodiment shown, which pattern is particularly easily captured by the sensor 7. If the sensor 7 captures the pattern 11, an object 8 located in front of it can be particularly accurately identified and this improves the reliability of error status detection.

In this case, the reference sign 12 shows symbolically a communication interface which can be used with an optional modification of the invention to transmit the results of the evaluations further.

So that a status detection works perfectly, even with a very dirty liquid, it can be provided that next to the intake connection 5 for drawing up the liquid to be pumped there is a supply connection 13 arranged on the suction side of the pump arrangement 1, via which a clear liquid, for example clear water, is introduced into the pump 1 where necessary, for example during or shortly before a photo is taken by the sensor 7.

Figure 2:
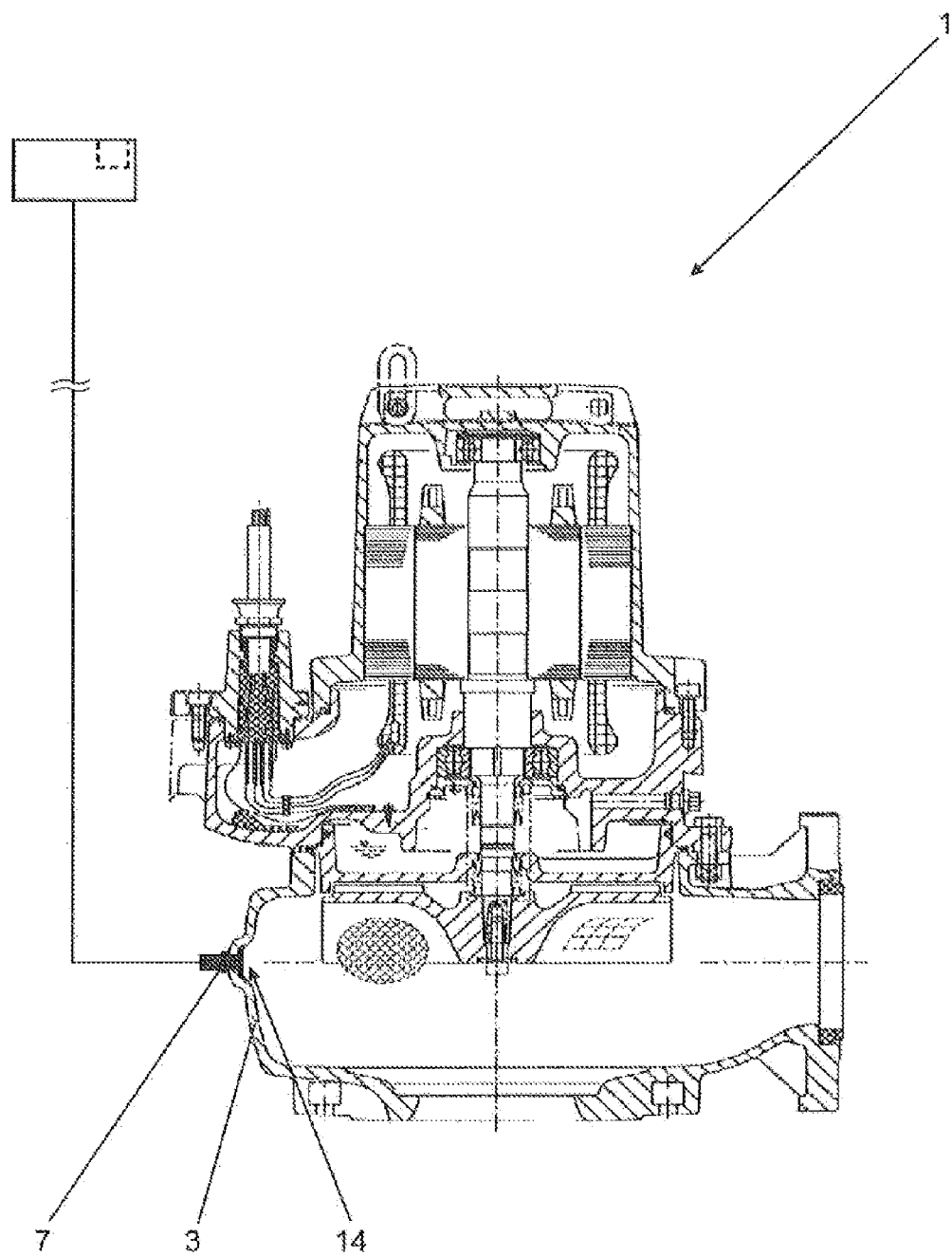
FIG. 2 shows a sectional view of a further pump according to an embodiment of the invention with the sensor.

FIG. 2 shows a further embodiment of the pump arrangement 1, in which the sensor 7 is arranged in a region 14 set back from the flow chamber 2. Consequently, the sensor 7 is in contact with the conveying medium, but is better protected from abrasive wear, mechanical impact by the solids contained in the medium, and contamination and sedimentation. The recessed region is shown in FIG. 2 as a concavity in the pump housing. Alternatively, the recessed region 14 can be produced by mechanical processing, in particular by machining, of the inside of the pump housing 3.

Figure 3:
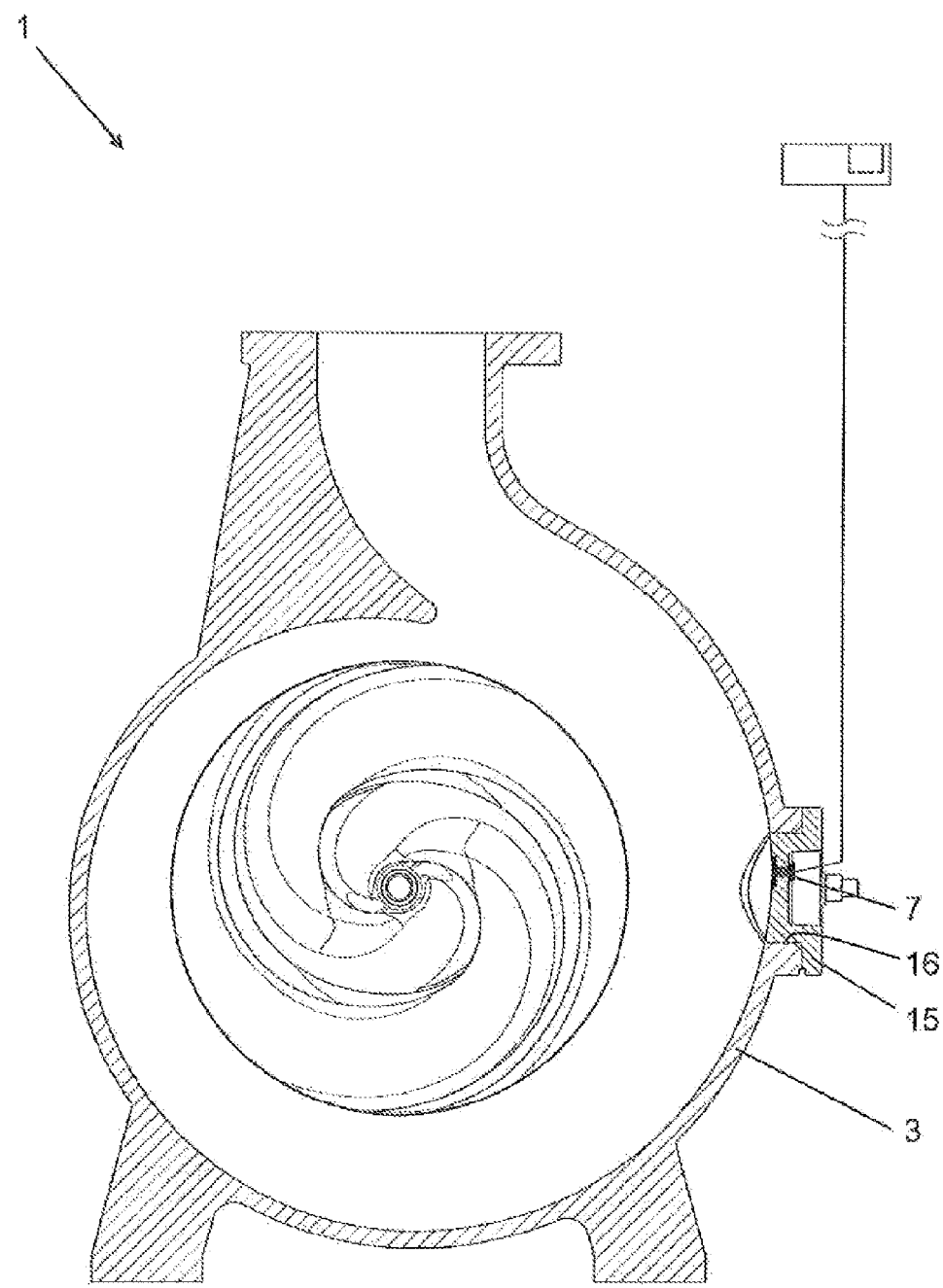
FIG. 3 shows a sectional view of a further pump according to an embodiment of the invention with the sensor.

FIG. 3 shows a vertically installed pump arrangement 1 in which the sensor 7 is arranged in a cover 15 for closing a so-called cleaning hole 16. This means that a bore in the pump housing 3 can be dispensed with.

It is self-evident that a recessed region, similar to the region 14 shown in FIG. 2, can be provided in the cover 15. In addition, it is possible for the pump arrangements 1 shown in FIGS. 1 and 2 to be equipped with a cover 15 according to FIG. 3.

In order to illuminate the detection range of the sensor 7, a lighting means which is not depicted in the figures can be provided in and/or on the pump housing 3 or on the sensor 7 itself.

A placement of the sensor 7, the lighting means, and/or the micro-pump may, in addition, also be provided at other points suitable therefor in or on the pump housing 3, for example close to the intake connection 5 and/or close to the delivery connection 6. FIGS. 1 to 3 each show a single-stage pump arrangement with an impeller 4 expelling in a radial direction. The invention may also be provided in a pump arrangement 1, for example, which has a multi-stage design and/or is provided with an impeller 4 expelling in an axial or semi-axial direction.

The supply connection 14 described in FIG. 1 can also be used in the different embodiments of pump arrangements 1.

The invention claimed is:

1. A pump arrangement for conveying a liquid, comprising:
    a pump housing;
    an impeller rotatably arranged about a center of rotation in the pump housing;
    a sensor; and
    a micro-pump configured to rinse and actively remove residues accumulated in front of a sensor surface of the sensor, wherein
        the sensor is a 2D or a 3D sensor configured to sense a surface of the impeller, and
        the sensor is arranged one or both of on and in the pump housing, facing the surface of the impeller.

2. The pump arrangement as claimed in claim 1, wherein the sensor is configured to determine a distance from the sensor to the impeller by time-of-flight.

3. The pump arrangement as claimed in claim 1, wherein the sensor is configured to determine a distance from the sensor to the impeller by phase-difference.

4. The pump arrangement as claimed in claim 1, wherein the sensor is configured to determine a distance from the sensor to the impeller by frequency-modulated continuous waves.

5. The pump arrangement as claimed in claim 1, wherein the sensor is one or more of an optical sensor, an optical 2D sensor, an optical 3D sensor, a 2D ultrasound sensor, a 3D ultrasound sensor, a MIMO (multiple-input multiple-output) radar sensor, a 2D laser distance sensor and a 3D laser distance sensor.

6. The pump arrangement as claimed in claim 1, wherein a characteristic pattern detectable by the sensor is present on the surface of the impeller at a predetermined impeller rotational position.

7. The pump arrangement as claimed in claim 6, wherein the characteristic pattern detectable by the sensor is a 2D pattern or a 3D pattern.

8. The pump arrangement as claimed in claim 1, further comprising:
    a light generator configured to illuminate a detection range of the sensor,
    wherein the light generator is arranged on with the sensor or one or both of in and on the pump housing.

9. The pump arrangement as claimed in claim 8, wherein the light generator is configured to emit intermittent light impulses which are synchronized with a rotational speed of the impeller.

10. The pump arrangement as claimed in claim 1, further comprising:
an ultrasound micro-actuator configured to generate an ultrasound shaking motion of one or both of a sensor surface of the sensor and a portion of the pump housing such that a layer of dirt deposited on the sensor surface is one or both of broken up and prevented from forming on the sensor surface.

11. The pump arrangement as claimed in claim 1, further comprising:
an intake connection configured to receive the liquid being conveyed, and
a supply connection on a suction side of the pump configured to supply clean water into the liquid being conveyed such that murkiness in the fluid being conveyed is reduced between the sensor and the surface of the impeller the sensor faces.

12. The pump arrangement as claimed in claim 1, further comprising:
a control unit (9),
wherein the control unit is configured to receive and analyze data received from the sensor to identify the presence of at least one of blockage, entanglement, cavitation, mechanical damage, or vibrations.

13. A method for detecting a blockage in a pump arrangement, the pump arrangement including a pump housing, an impeller rotatably arranged about a center of rotation in the pump housing and a sensor, the sensor being a 2D or a 3D sensor configured to sense a surface of the impeller and being arranged one or both of on and in the pump housing, facing the surface of the impeller, the method comprising the steps of:
producing with the sensor data associated with the surface of the impeller the sensor faces;
analyzing using a control unit the data associated with the impeller produced by the sensor;
placing a micro-pump configured to rinse and actively remove residues accumulated in front of a sensor surface of the sensor; and
determining with the control unit whether the analyzed data associated with the impeller produced by the sensor indicates the presence of at least one of the blockage, entanglement, cavitation, mechanical damage, or vibrations.

14. The method as claimed in claim 13, wherein the data associated with the impeller produced by the sensor is images of the impeller.

15. The method as claimed in claim 14, wherein the images of the impeller are produced by the sensor after clean water is added on a suction side of the pump arrangement to reduce any murkiness in the liquid present in the vicinity of the impeller during the sensor's taking images.

16. The method as claimed in claim 14, wherein the images taken by the sensor are of a portion of the impeller provided with a characteristic pattern.

17. The method as claimed in claim 14, wherein the images taken by the sensor are synchronized with a rotational speed of the impeller.

18. The method as claimed in claim 16, wherein the images taken by the sensor are synchronized with a rotational speed of the impeller.

19. The method as claimed in claim 13, further comprising:
producing a signal by the control unit determining the presence of at least one of blockage, entanglement, cavitation, mechanical damage, or vibrations;
switching-on or off of the pump arrangement in response to the control unit signal.

* * * * *